United States Patent
Lachwani et al.

(10) Patent No.: US 9,776,041 B1
(45) Date of Patent: Oct. 3, 2017

(54) USER PERFORMANCE ANALYSIS SYSTEM

(71) Applicants: Anya Manish Lachwani, Los Altos, CA (US); Manish Lachwani, Los Altos, CA (US)

(72) Inventors: Anya Manish Lachwani, Los Altos, CA (US); Manish Lachwani, Los Altos, CA (US)

( * ) Notice: Subject to any disclaimer, the term of this patent is extended or adjusted under 35 U.S.C. 154(b) by 0 days.

(21) Appl. No.: 14/980,306

(22) Filed: Dec. 28, 2015

Related U.S. Application Data

(60) Provisional application No. 62/099,298, filed on Jan. 2, 2015.

(51) Int. Cl.
G08C 19/22 (2006.01)
H04Q 9/00 (2006.01)
A63B 24/00 (2006.01)
G08B 5/36 (2006.01)

(52) U.S. Cl.
CPC ............ *A63B 24/0062* (2013.01); *G08B 5/36* (2013.01); *A63B 2220/20* (2013.01); *A63B 2220/40* (2013.01); *A63B 2220/89* (2013.01)

(58) Field of Classification Search
CPC ................................................ A63B 24/0062
USPC .................................................... 340/870.07
See application file for complete search history.

(56) References Cited

U.S. PATENT DOCUMENTS

| | | | |
|---|---|---|---|
| 9,241,635 B2 * | 1/2016 | Yuen | A61B 5/02405 |
| 2007/0000154 A1 * | 1/2007 | DiBenedetto | A43B 1/0036 36/132 |
| 2012/0083705 A1 * | 4/2012 | Yuen | A61B 5/0002 600/508 |
| 2013/0006583 A1 * | 1/2013 | Weast | A61B 5/112 702/189 |
| 2013/0217979 A1 * | 8/2013 | Blackadar | A61B 5/0024 600/301 |
| 2014/0135612 A1 * | 5/2014 | Yuen | A61B 5/02405 600/407 |
| 2014/0358473 A1 * | 12/2014 | Goel | A61B 5/1118 702/141 |
| 2016/0322078 A1 * | 11/2016 | Bose | G11B 27/031 |
| 2016/0346584 A1 * | 12/2016 | Schneider | A61B 5/1123 |
| 2016/0351774 A1 * | 12/2016 | Schneider | H01L 35/32 |
| 2016/0351775 A1 * | 12/2016 | Schneider | H01L 35/32 |
| 2016/0351776 A1 * | 12/2016 | Schneider | H01L 35/30 |

* cited by examiner

*Primary Examiner* — Santiago Garcia
(74) *Attorney, Agent, or Firm* — Lindauer Law, PLLC

(57) ABSTRACT

A system may use a sensor device affixed to the user or an article of clothing of the user to provide information on performance of an activity. For example, a sensor device may be affixed to a portion of the laces on footwear of the user. Acquired data from the sensor device may be processed to provide analysis information to the user about the performance.

20 Claims, 7 Drawing Sheets ized by the appended claims. The headings used herein
USER PERFORMANCE ANALYSIS SYSTEM

PRIORITY

This application claims priority to U.S. Provisional Patent Application Ser. No. 62/099,298 filed on Jan. 2, 2015, titled "User Performance Analysis System" with first named inventor Anya Manish Lachwani, the contents of which are incorporated by reference into the present disclosure.

BACKGROUND

A wide variety of activities involve movement, such as everyday living, athletics, and so forth. Data about performance of these activities may be useful. For example, children may be encouraged to participate in a certain amount of physical activity every day as part of a healthy lifestyle.

BRIEF DESCRIPTION OF DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
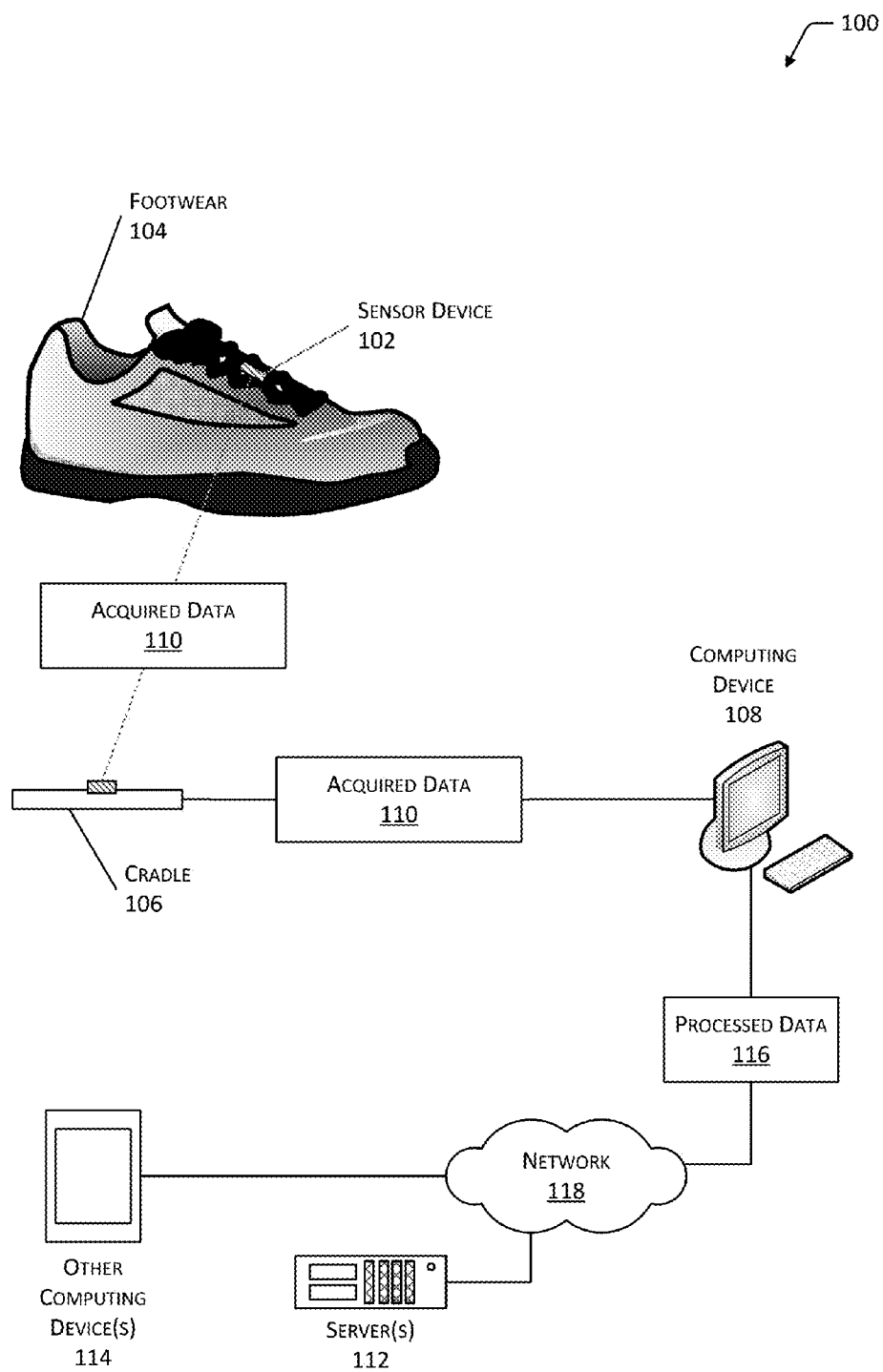
FIG. 1 illustrates a system for acquiring and processing information about performance of a user during an activity.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include," "including," and "includes" mean "including, but not limited to".

DETAILED DESCRIPTION

One or more sensors may be used to acquire data that may be used for various purposes. The acquired data may include information associated with a user. For example, the acquired data may include, but is not limited to, location of a user, rate at which the user is moving, vital signs of the user, and so forth. The acquired data may also include information about the environment surrounding the one or more sensors. For example, the acquired data may include, but is not limited to, temperature, barometric pressure, sound level or intensity, and so forth.

This disclosure describes a system including devices and techniques that may use a sensor device to acquire data. The acquired data may provide information that is useful to assess performance of a user associated with the sensor device, performance of equipment such as clothing or environmental control equipment, and so forth. The acquired data may be used to generate a summary value. For example, the summary value may comprise a sum of individual values associated with motion of the user, wherein each of the individual values exceeds a threshold level.

The sensor device may be configured to be clipped or otherwise affixed to an article of clothing, such as footwear. During performance of an activity, the sensor device may use one or more sensors to gather information and store acquired data, a summary value, or other information in memory. At a later time, the acquired data, summary value, or other information may be transferred from the memory of the sensor device to another device, such as a computing device. For example, the sensor device may be placed in a cradle that that provides electrical power, data connectivity with a personal computer or tablet, and so forth. In another example, the sensor device may use wireless communication to transfer the summary value to an administrative computing device.

The acquired data may processed by another device. For example, the cradle, computing device, or other device may produce processed data. For example, the acquired data may be decompressed, filtered, and so forth.

In one implementation, the sensor device may be worn by a user (player) during participation in an athletic activity, such as playing basketball. The processed data associated with the athletic activity may be used to provide information about user performance, such as average speed, ability to start and stop quickly, position on the basketball court, and so forth.

In other implementation, the devices and techniques may be used in other activities. For example, the sensor device may be configured for users participating in athletic activities including baseball, football, soccer, hockey, running, jogging, and so forth. In other implementations, the devices and techniques may be used for other activities including medicine, military, recreation, and so forth. For example, the sensor device may be used to acquire information for medical treatment purposes, such as occupational therapy, physical therapy, and so forth. In another example, the sensor device may be configured for military purposes including physical training, military exercises, and so forth. Other uses for the devices and techniques not described may be included as falling within the scope of the present disclosure.

The sensor device may be initialized when connected to a cradle. The cradle may be configured to provide electrical power to the sensor device, such as charging a power source of the sensor device. The cradle may also provide data connectivity, such as providing a Universal Serial Bus (USB) connection between the sensor device and a computing device. The cradle may comprise a structure to support and hold the sensor device. Once the sensor device is initialized, the user may remove the sensor device from the cradle for use. For example, the sensor device may be worn by clipping it to an object the user is wearing, such as footwear, shorts, and so forth. In other implementations, the sensor device may be initialized upon attachment to an object, responsive to activation of a button, at a particular time interval, and so forth.

The sensor device may be configured to detect that it has been clipped onto or otherwise affixed to an object. For example, a proximity sensor may indicate the presence of an object, a switch may indicate that a clip mechanism of the sensor device has been displaced, and so forth. Once the sensor device is determined to be clipped or otherwise affixed to an object, the sensor device may begin acquiring sensor data from one or more sensors. The one or more sensors within the sensor device may include, but is not limited to, location sensors, microphones, temperature sensors, accelerometers, gyroscopes, magnetometers, weight sensors, and so forth. Of these sensors, motion sensors may include the accelerometers, gyroscopes, magnetometers, location sensors, and so forth. The data collected by the one or more sensors within the sensor device is stored in the memory of the sensor device as acquired data. In some implementations, the acquired data may be otherwise processed by the sensor device. For example, the sensor device may use the acquired data to generate a summary value. Continuing example, the accelerometer may provide a serialized stream of data indicative of a motion vector including a time. The motion vector and time may be used to generate a scalar value representative of motion.

The acquisition of data by the sensor device may be configured to continue until the sensor device is unclipped from the object (such as removed from the user's shoelaces), when the sensor device has not moved for a threshold amount of time, when available power at the sensor device is below a threshold amount, and so forth. For example, data acquisition may stop when available power is less than 1% of total capacity. In other implementations, the rate of data acquisition, number of sensors that are active, and so forth, may change based on available power. For example, the sample rate of data from the sensors may be decreased when available power is below 3%.

In some implementation, when the sensor device has stopped acquiring data due to inactivity or too little motion, but is still clipped on the object, the sensor device may resume acquiring data if movement of the sensor device is detected. For example, after being on the bench and resuming play, the sensor device affixed to the user's footwear may resume data collection. In other implementations, a sample rate to acquire data may vary based on the acquired data. For example, when the level of motion represented by the acquired data is below a threshold level, the sensor device may acquire data at a first sample rate. Continuing the example, as the level of motion increases and is above the threshold level, the sensor device may transition to acquire data at a second sample rate, where the second sample rate is greater than the first sample rate.

In one implementation, when the sensor device is connected to the cradle, the acquired data, summary value, or other information may be transferred from the sensor device to the computing device, which may also be connected to the cradle. In another implementation, the sensor device may transfer acquired data, summary value, or other information to the computing device using a communication device. In some implementations, transfer of one or more of the acquired data, the summary value, or other information may be made wirelessly. For example, the sensor device may use an optical data transfer mechanism by modulating the output of a single element output device, such as a light-emitting diode.

The computing device uses a software program to generate processed data, which may then be analyzed. Analysis of the acquired data may include determining the best position for the user on the basketball court, areas for personal improvement, difference in crowd responses between home and away games, and so forth. The processed data is transferred to one or more servers via a network. The processed data may be provided to other computing devices connected to the one or more server via the network. Providing the processed data to other computing devices allows the user and other users including coaches, teammates, and so forth, to access processed data for improving future performance.

FIG. 1 illustrates a system 100 for acquiring and processing information about performance of a user during an activity. A sensor device 102 may be affixed or otherwise physically coupled to an object such as an article of clothing, piece of athletic or protective equipment, and so forth. For example, the sensor device 102 may be clipped to footwear 104, such as a shoe. The sensor device 102 may be clipped, laced, tied, bonded, retained within a pocket, and so forth, by or to the object. For example, the sensor device 102 may clip to at least a portion of the laces of the footwear 104. The sensor device 102 may be configured to be shock resistant, water resistant, and so forth. In some implementations, the sensor device 102 may also be known as a wearable motion tracking device.

The sensor device 102 may be configured to couple to a cradle 106. The cradle 106 may provide one or more of power, communications, cleaning, and so forth. For example, the cradle 106 may provide data communication between the sensor device 102 when placed therein and a computing device 108. The communication between the cradle 106 and the computing device 108 may be wired (such as a USB connection) or wireless (such as Bluetooth®, Wi-Fi®, and so forth). For example, the cradle 106 may use a microUSB connector to couple to the sensor device 102. In some implementations, the cradle 106 may use a wireless charging mechanism to provide electrical power to the sensor device 102. For example, the cradle 106 may include an inductive transmitter and the sensor device 102 may comprise an inductive receiver.

During operation of the sensor device 102, sensor data from one or more sensors may be stored as acquired data 110. In some implementations, the sensor device 102 may further process the acquired data 110 and generate a summary value. The summary value may comprise information indicative of motion by the sensor device 102 that exceeds a threshold value.

The cradle 106 may be used to transfer information such as the acquired data 110 to the computing device 108. The computing device 108 may comprise a desktop computer, laptop computer, tablet, smartphone, personal computer, portable computer, and so forth. In other implementations, the acquired data 110, summary value, or other information may be sent wirelessly.

The sensor device 102 may be initialized when the sensor device 102 is connected to the cradle 106, which is also connected to a computing device 108. When the sensor device 102 is initialized, a timer within the sensor device 102 may be set to a determined date and time. The cradle 106 may also provide power to the sensor device 102 when it is connected to the computing device 108 or an external power socket. Initialization may comprise one or more of restarting a processor of the sensor device 102, resetting the sensor device 102 to a predetermined state, booting an operating system on a processor of the sensor device 102, and so forth.

In some implementations, the sensor device 102 may be initialized, reset, or otherwise have its operation modified responsive to one or more conditions or inputs. For example, activation of a button on the sensor device 102, expiration of a predetermined time period, determination that the sensor device 102 is no longer affixed to the object, and so forth, may result in a sensor device 102 to be reset.

The sensor device 102 may be worn by a user. The user may include a human, animal, robot, and so forth. The user may clip the sensor device 102 to an object that the user is wearing, such as the user's footwear 104. The footwear 104 may include, but is not limited, to shoes, sandals, socks, boots, and so forth.

When the sensor device 102 has been clipped or otherwise affixed to the object, the sensor device 102 may begin to acquire data from one or more sensors, store the acquired data 110, calculate a summary value, and so forth. For example, after clipping on the sensor device 102 to the user's footwear 104, the sensor device 102 may begin to detect and collect acquired data 110 about the user and the surrounding environment. In some implementations, the acquired data 110 may be obtained and used to calculate a summary value. The sensor device 102 may be configured to detect and collect various types of acquired data 110.

The obtained acquired data 110 may include location, speed, distance, and so forth, of the user. The acquired data 110 may also include temperature, wind pressure, sound levels, and so forth, of the surrounding environment. The acquired data 110 may be stored in memory of the sensor device 102 until the sensor device 102 is reconnected to the cradle 106 connected to the computing device 108.

The acquired data 110 may be transferred from the sensor device 102 to the computing device 108. The computing device 108 may be coupled to one or more networks 118. The network 118 may include personal area networks (PANS), local area networks (LANs), wireless LANs (WLANs), wide area networks (WANs), wireless WANs, and so forth. The networks 118 may, in turn, be coupled to one or more servers 112 or other computing devices 114. One or more of the computing device 108, the server 112, or the other computing device 114 may be configured to process the acquired data 110 as transferred from the sensor device 102 to generate processed data 116.

The processed data 116 may be used to generate information about performance of the user. In some implementations, the processed data 116 may be combined or fused with information from other sources, such as video of the activity, data from the sensor devices 102 of other users, and so forth.

Figure 2:
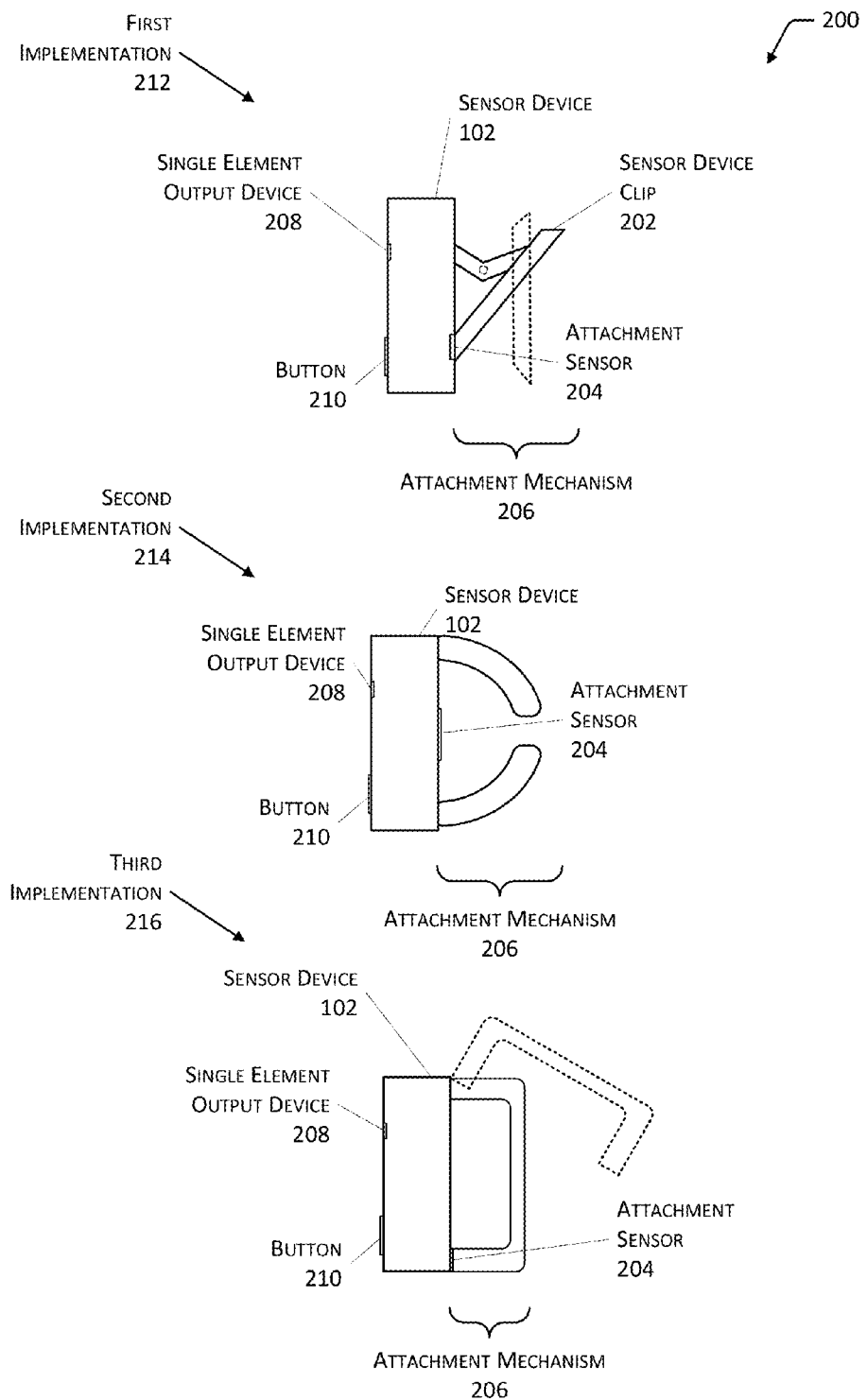
FIG. 2 illustrates a side view of some implementations of a sensor device configured to acquire data.

FIG. 2 illustrates a side view 200 of some implementations of a sensor device 102. Depicted by way of illustration, and not necessarily as limitation, are a first implementation 212, a second implementation 214, and a third implementation 216.

As depicted in the first implementation 212, the sensor device 102 may include an attachment mechanism 206, such as the sensor device clip 202. In the second implementation 214 and the third implementation 216, other types of attachment mechanisms 206 are depicted. The second implementation 214 in FIG. 2 depicts an attachment mechanism 206 comprising a pair of arcuate arms. The third implementation 216 in FIG. 2 depicts an attachment mechanism 206 comprising a loop or "D" section. For example, a shoe lace or other portion of the object may pass through this loop. In some implementations, the loop may open, as indicated by the broken lines. In other implementations, the loop may be permanently affixed to the sensor device 102. In still other implementations, a retention loop, hook and loop fastener, magnet, snap, or other mechanisms may be used to affix or retain the sensor device 102 to the object.

An attachment sensor 204 may be used to provide data indicative of when the sensor device clip 202 is clipped to an object, such as an article of clothing the user is wearing. The object may include the user's footwear 104 or other article of clothing worn by the user. The attachment sensor 204 may comprise an electrical contact, a switch, a proximity sensor, or other mechanism.

In some implementations, the sensor device 102 may be configured without buttons, touch interface, or other overt user interface devices. This configuration may improve durability by reducing components that are subject to shock or damage. The attachment sensor 204 allows the sensor device 102 to detect a clip on and off. The attachment sensor 204 may trigger a general purpose input/output (GPIO) interrupt. As described elsewhere, this may be used to start or stop data acquisition.

In other implementations, the sensor device 102 may include one or more buttons 210. For example, the button 210 may be used to reset or reinitialize sensor device 102.

In some implementations, when the sensor device clip 202 of the sensor device 102 is clipped on to an object the user is wearing, the sensor device 102 may begin to obtain and collect data. For example, when a user attaches the sensor device 102 by the sensor device clip 202 to their footwear 104, the sensor device 102 uses data from the attachment sensor 204 to begin acquisition of data from one or more sensors. In other implementations, when the sensor device 102 is unclipped or otherwise removed from an object the user is wearing, the sensor device 102 stops detecting and acquiring data. For example, as depicted in the first implementation 212 of FIG. 2, the sensor device clip 202 is not clipped on to an object worn by the user. In this condition, the sensor device 102 may be configured to not detecting or collecting any data about the user or the surrounding environment.

In still other implementations, the sensor device 102 may stop detecting or acquiring data while the sensor device clip 202 is clipped on to an object worn by the user. For example, the sensor device 102 may stop detecting and acquiring data about the user and the surrounding environment when a certain amount of time has elapsed and there has been no movement by the user with the sensor device 102 attached to their footwear 104. Continuing the example, the sensor device 102 may resume detecting and acquiring data after stopping when movement is detected by the sensor device 102 attached to the footwear 104 of the user. As another example, the sensor device 102 may stop detecting and acquiring data about the user and the surrounding environment when the power supply in the sensor device 102 attached to the footwear 104 of the user reaches 1% or less.

In some implementations, data from the attachment sensor 204 may be stored in the memory. For example, a clip on or clip off event as determined by the attachment sensor 204 may be recorded and included in the acquired data 110.

In some implementations, the sensor device 102 may include an output device, such as a single element display device 208. The single element display device 208 may provide a visual indicator of information such as power level, operational status, data obtained, and so forth. For example, the single element output device 208 may comprise a light-emitting diode that is configurable to present three different colors. When the sensor device 102 determines the summary value is less than a minimum threshold value of the motion of the device, the single element output device 208 is activated to emit a first color, such as red. When the sensor device 102 determines the summary value is greater than the minimum threshold value and less than an intermediate threshold value of the motion of the device, the single element output device 208 is activated to emit a second color, such as yellow. When the sensor device 102 determines the summary value is greater than the intermediate threshold value, the single element output device 208 is activated to emit a third color, such as green.

Figure 3:
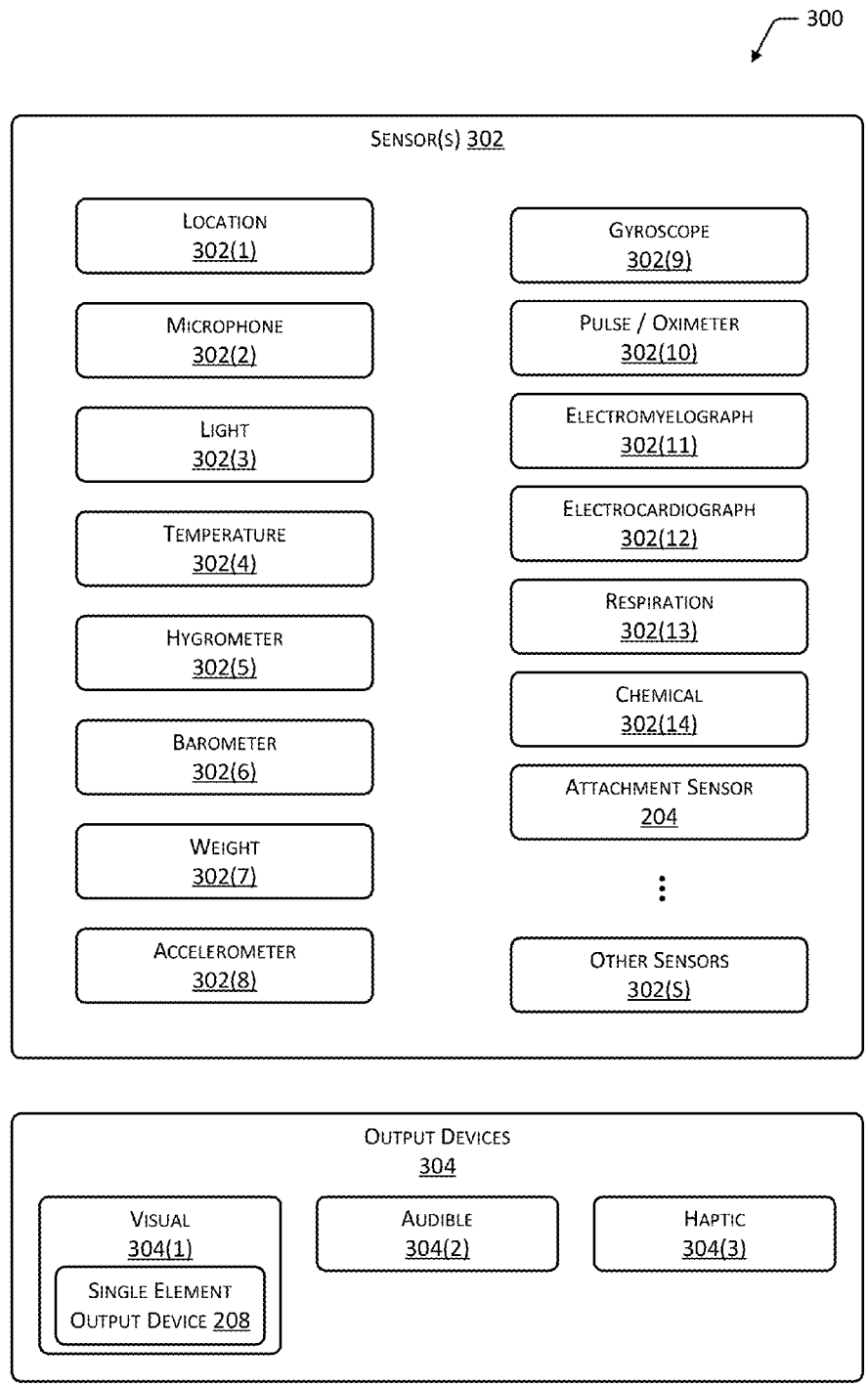
FIG. 3 is a block diagram illustrating one or more sensors and output devices of the sensor device, according to some implementations.

FIG. 3 is a block diagram 300 illustrating one or more sensors and output devices of the sensor device 102, according to some implementations. The sensor device 102 may comprise one or more sensors 302, which are configured to detect and collect data about the user and the surrounding environment of the sensor device 102.

The sensors 302 may include one or more location sensors 302(1) configured to detect and collect data about the location of the user. The location sensors 302(1) may include, but are not limited to, radionavigation devices such as systems using terrestrial or satellite-based navigation systems. A satellite-based navigation system may include one or more of a Global Positioning System (GPS) receiver, a Global Navigation Satellite System (GLONASS) receiver, a Galileo receiver, an Indian Regional Navigational Satellite System, and so forth. For example, the location sensors 302(1) may be configured to detect and collect location data, such as latitude and longitude, about the location where the user is participating in a basketball game. In other implementations, the location sensors 302(1) may use other techniques such as optical signals to determine location.

The sensors 302 may also include one or more microphones 302(2). The one or more microphones 302(2) may be configured to acquire sound data about the surrounding environment of the sensor device 102. For example, the one or more microphones 302(2) may be configured to detect and collect data during the basketball game of the crowd response at the location of the basketball game.

One or more light sensors 302(3) may be included in the sensors 302. The one or more light sensors 302(3) may be configured to detect and collect data associated with ambient lighting conditions in the surrounding environment of the sensor device 102. For example, the one or more light sensors 302(3) may be configured to detect and collect data about the ambient lighting conditions at the location of the basketball game. The one or more light sensors 302(3) may be sensitive to one or more wavelengths, including infrared light, visible light, ultraviolet light, and so forth.

The sensors 302 may include one or more temperature sensors 302(4). The one or more temperatures sensors 302(4) may be configured to acquire temperature data about the surrounding environment of the sensor device 102. For example, the one or more temperatures sensors 302(4) may be configured to detect and collect temperature data at the location of the basketball game. In other implementations, instead of or in addition to, detecting and collecting the temperature data of the surrounding environment, the temperature data detected and collected may be of the user.

The sensors 302 may include one or more hygrometers 302(5). The one or more hygrometers 302(5) may be configured to acquire humidity data about the surrounding environment of the sensor device 102. For example, the one or more hygrometers 302(5) may be configured to detect and collect humidity data at the location of the basketball game.

The sensors 302 may include one or more barometers 302(6). The one or more barometers 302(6) may be configured to acquire atmospheric data about the surrounding environment of the sensor device 102. For example, the one or more barometers 302(6) may be configured to detect and collect atmospheric data at the location of the basketball game.

The sensors 302 may include one or more weight sensors 302(7). The one or more weight sensors 302(7) may be configured to acquire weight data about the user of the sensor device 102. For example, the one or more weight sensors 302(7) may be configured to detect and collect weight data about the weight of the footwear 104 that the sensor device 102 is affixed to by the sensor device clip 202.

One or more accelerometers 302(8) may also be included in the sensors 302. The one or more accelerometers 302(8) may be configured to detect and collect acceleration data, including the direction and magnitude, about the sensor device 102. For example, the one or more accelerometers 302(8) may be configured to determine the speed and direction of the user wearing the sensor device 102 during a basketball game.

The sensors 302 may include one or more gyroscopes 302(9). The one or more gyroscopes 302(9) may be configured to detect and collect orientation data. For example, the one or more gyroscopes 302(9) may be configured to detect and collect orientation data of the user wearing the sensor device 102 during the basketball game.

Some sensors 302 may acquire information about vital signs of the user. A pulse/oximeter 302(10) may be configured to acquire information about the user's cardiac pulse, blood oxygen saturation, and so forth. An electromyelograph 302(11) may acquire information about electrical activity associated with muscle contractions. An electrocardiograph 302(12) may acquire information about the cardiac rhythms of the user. A respiration sensor 302(13) may measure the users respiratory patterns. A chemical sensor 302(14) may be configured to detect one or more chemical species, such as that emitted by the user in the form of sweat or exhalation, or otherwise present in the environment. Other sensors 302(S) may also be included in the sensors 302. Other sensors 302(S) may include one or more proximity sensors, magnetometers, buttons, switches, and so forth. As used in this disclosure, letters in parenthesis such as "(S)" indicate an integer value.

Of the sensors 302, those sensors which provide information about the movement of the sensor device 102 may be referred to as motion sensors. The motion sensors may include, but are not limited to, the accelerometers 302(8), gyroscopes 302(9), magnetometers, location sensors 302(1), and so forth.

The attachment sensor 204, as described above, provides information about a state of the clip or other retaining device. This information may be indicative of whether the sensor device 102 is affixed to an object or not.

Output devices 304 may be used by the sensor device 102 to provide information to the user. The output devices may be visual 304(1), audible 304(2), haptic 304(3), or a combination thereof. For example, the visual 304(1) output device may the single element display device 208. The single element display device 208 may comprise a mechanism that provides visual indicia that may be seen by the user. For example, the single element display device 208 may comprise one of a light-emitting diode, an electroluminescent element, an incandescent lamp, a fluorescent lamp, a quantum dot, an electrophoretic element, a cholesteric element, a microelectromechanical element, an interferometric element, and so forth. Compared to a bitmapped or raster display that is able to generate an image from one or more picture elements, the single element display device 208 may present visual indicia having a consistent area but changing in some other characteristic such as elimination, color, reflectivity, and so forth.

The audible 304(2) output device may comprise a speaker, buzzer, beeper, and so forth. The haptic 304(3) output devices may comprise an electrode, motor, piezoelectric device, and so forth.

Figure 4:
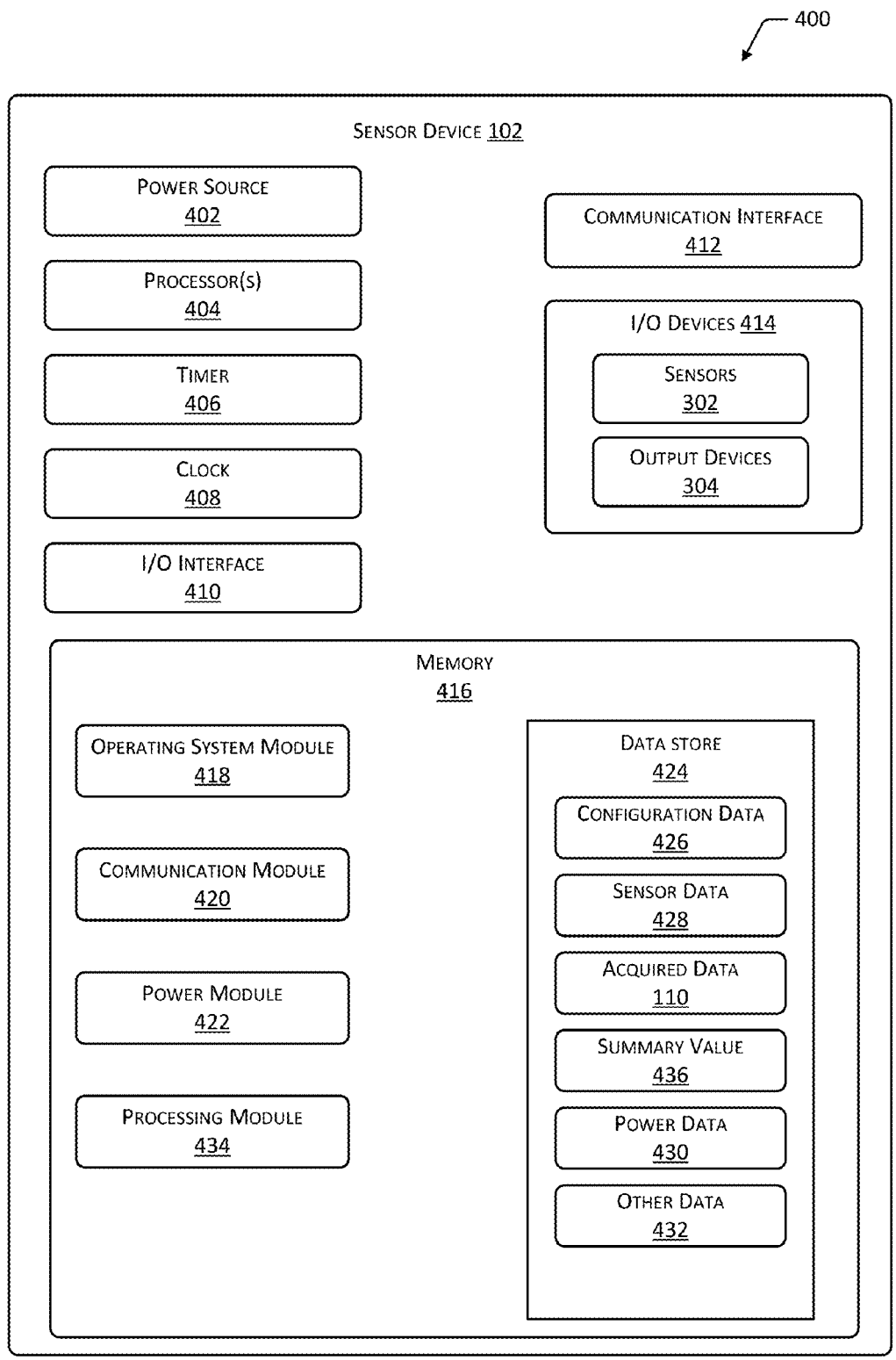
FIG. 4 is a block diagram of the sensor device configured to acquire data, according to some implementations.

FIG. 4 illustrates a block diagram 400 of the sensor device 102 configured to detect and collect data of the user and the surrounding environment. In some implementations, the sensor device 102 may also be known as a wearable motion tracking device.

The sensor device 102 may include one or more power sources 402 including, but not limited to, a single use battery, a rechargeable battery, capacitor, fuel cell, photovoltaic cell, and so forth. The power source 402 provides electrical energy to operate the sensor device 102. The power source 402 may receive electricity from an external source using one or more contacts, a wireless power receiver, and so forth.

The sensor device 102 may include one or more hardware processors 404 (processors) configured to execute one or more stored instructions. The processors 404 may comprise one or more cores.

The sensor device 102 may also include one or more timers 406. The timer 406 may comprise a high precision event timer (HPET) or high resolution timer (HRT) having one or more counters. For example, the timer 406 may include a 32 or 64 bit counter counting at a frequency of at least 5 megahertz (MHz). The timers 406 may be configured to count up, down, or both.

The counting provided by the one or more timers 406 may occur in one or more of two modes: a timer interrupt mode where the timer 406 is polled or in an interrupt mode based on the interrupt request (IRQ) status register triggers. In the timer interrupt mode, after the timer IRQ status bit is cleared, the IRQ status register is checked for the presence of another interrupt bit.

A clock 408 may be included to provide information such as date, time, and so forth. For example, the clock 408 may comprise a real-time clock. In some implementations, the timer 406 may be used as the clock 408, or vice versa.

The sensor device 102 may include one or more input/output (I/O) interfaces 410 to allow the processor 404 to communicate with another device, such as the cradle 106. The I/O interface 410 may comprise Inter-Integrated Circuit (I2C), Serial Peripheral Interface (SPI), Universal Serial Bus (USB) as promulgated by the USB Implementers Forum, RS-232, and so forth.

In some implementations, the sensor device 102 may include one or more communication interfaces 412. For example, the communication interfaces 412 may be compatible with Ethernet, Wi-Fi®, Bluetooth®, ZigBee®, 3G, 4G, LTE, and so forth.

The sensor device 102 may include one or more I/O devices 414 including one or more sensors 302, output devices 304, and so forth.

The sensor device 102 may also include a memory 416 comprising one or more computer-readable storage media (CRSM). The CRSM may be any one or more of an electronic storage medium, a magnetic storage medium, an optical storage medium, a quantum storage medium, a mechanical computer storage medium, and so forth. The memory 416 provides storage of computer-readable instructions, data structures, program modules, and other data for the operation of the sensor device 102. A few example functional modules are shown stored in the memory 416 and executed on the processor 404, although the same functionality may alternatively be implemented in hardware, firmware, or as a system on a chip (SoC). In one implementation, the memory 416 may include an embedded multimedia card (eMMC).

The memory 416 may include at least one operating system (OS) module 418. The OS module 418 is configured to manage hardware resource devices such as the I/O interfaces 410, the I/O devices 414, the communication interfaces 412, and provide various services to applications or modules executing on the processors 404. The OS module 418 may implement a variation of the Android™ operating system as promulgated by Google, Inc.; a variation of the Linux™ operating system as promulgated by Linus Torvalds; a variant of the FreeBSD™ operating system as promulgated by the FreeBSD Project; other UNIX™ or UNIX-like variants; the Windows® operating system from Microsoft Corporation of Redmond, Wash., USA; and so forth.

Also stored in the memory 416 may be one or more of the following modules. These modules may be executed as foreground applications, background tasks, daemons, and so forth.

A communication module 420 may be configured to establish communication with another device, such as the cradle 106, the computing device 108, the network 118, and so forth. The communications may be authenticated, encrypted, and so forth.

A power module 422 may be configured to manage the power use by the sensor device 102. The power module 422 may be configured to transition one or more of the processor 404, the I/O devices 414, and so forth, between a low power state and a high power state. In one implementation, the power module 422 may be configured to provide output using an output device 304 (such as flashing the single element display device 208) when available power capacity is less than or equal to 2% of total (maximum) power capacity. The power module 422 may then be configured to place the sensor device 102 into a shutdown mode when the available power capacity is less than or equal to 1%. In some implementations, a sample rate of the one or more sensors 302 may be determined based at least in part on the output from the power module 422.

A data store 424 may be stored in the memory 416. The data store 424 may use a flat file, database, linked list, tree, executable code, script, or other data structure to store information. In some implementations, the data store 424 or a portion of the data store 424 may be distributed across one or more other devices including the servers 112, network attached storage devices, and so forth.

The data store 424 may store configuration data 426. The configuration data 426 may specify sampling rates for one or more of the sensors 302, filter parameters for filtering which sensor data 428 to store as acquired data 110, power management parameters for use by the power module 422, threshold data, device identifier information, and so forth. For example, the threshold data may specify one or more thresholds used during operation of the device.

Sensor data 428 comprises information acquired by the one or more sensors 302. In some implementations, the "raw" sensor data 428 may be compared to filter parameters to determine whether information should be stored as acquired data 110, or discarded. In other implementations, the acquired data 110 may comprise all of the sensor data 428. In some implementations, the acquired data 110 may be written to the memory 416 with microsecond granularity.

The power data 430 comprises information about state of the power source 402, power consumption information, and so forth. The power data 430 may be stored in the memory 416.

Other data 432 may also be stored in the memory 416. For example, the other data 432 may include status data indicative of whether the attachment sensor 204 is in an open state, is in a closed state, timestamp or counter information as to when the state changed, and so forth.

The processing module 434 may be configured to perform one or more operations, such as obtaining the sensor data 428 from one or more of the sensors 302, generating the acquired data 110, generating summary value 436, and so forth. In one implementation, the summary value 436 may comprise a metric that is indicative of the motion of the sensor device 102 exceeding a threshold value. For example, summary value 436 may comprise a sum of scalar values based at least in part on output from the accelerometer 302(8). Values of the acquired data 110 that exceed a threshold value may be used to generate the summary value 436. Continuing the example, the summary value 436 may comprise a metric that is indicative of a summation of vigorous activity by the user.

The processing module 434 may be configured to provide output using one or more of the output devices 304. For example, the single element output device 208 may comprise light-emitting diode. The processing module 434 may determine the summary value 436 is less than a minimum threshold value. Responsive to this, the processing module 434 may activate the light-emitting diode to emit a first color. The processing module 434 may determine the summary value 436 is greater than a minimum threshold value and less than an intermediate threshold value. Responsive to this, the processing module 434 may activate the light-emitting diode to emit a second color. The processing module 434 may determine the summary value 436 is greater than the intermediate threshold value. Responsive to this, the processing module 434 may activate the light-emitting diode to emit a third color.

The processing module 434 may be configured to provide information to the user by way of the output device 304. For example, the single element output device 208 may be pulsed to provide flashes indicative of the summary value 436. Continuing the example, pulsing may be consistent with use of Morse code, or another technique to indicate a numeric or alphabetic value.

The processing module 434 may be configured to reset the sensor device 102. The reset may be initiated by one or more of activation of the button 210, expiration of a reset time period, or other condition. For example, sensor device 102 may clear out the acquired data 110 and the summary value 436 every 24 hours.

The reset may include the disregarding of previously stored sensor data 428, acquired data 110, summary value 436, and so forth. The disregarding may include, but is not limited to, deletion, reallocation, or other manipulations of the memory 416 storing this information. In some implementations, following the reset, the sample rate in which information is obtained from the sensors 302 may be changed.

The processing module 434 may use the status data. For example, responsive to a change in the status data from a closed state to an open state, the processing module 434 may initiate a reset. In another implementation, the processing module 436 may present information indicative of a count of changes in the status data within a threshold amount of time, since the last reset, and so forth, using one or more output devices 304, such as the single element output device 208. For example, the single element output device 208 may be activated to flash in a predetermined patterned indicative of change in status data.

Figure 5:
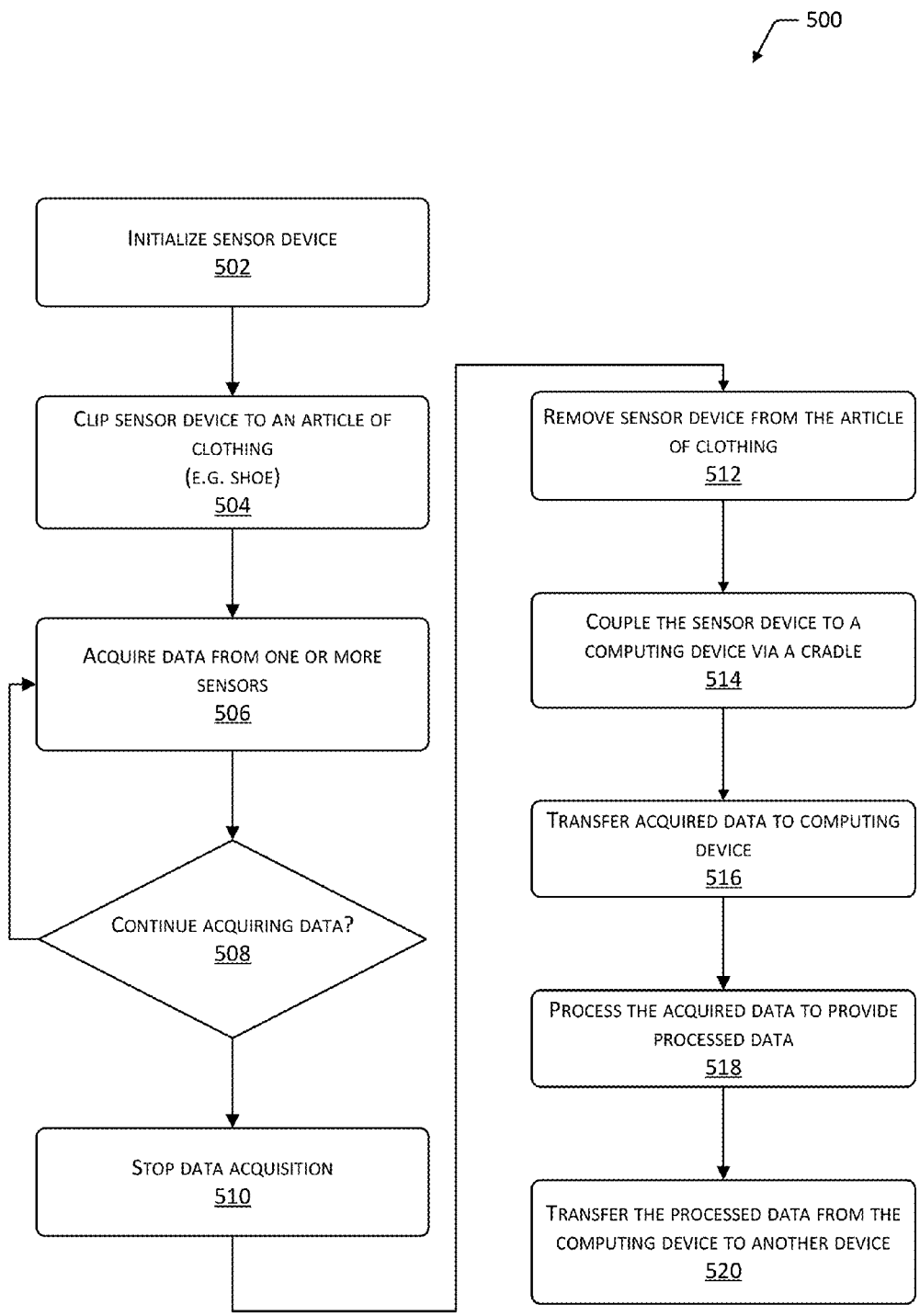
FIG. 5 illustrates a flow diagram of a process to acquire data using the sensor device, according to some implementations.

FIG. 5 illustrates a flow diagram 500 of a process of the sensor device 102 for detecting, collecting, transferring, and analyzing data about the user and surrounding environment.

At 502, the sensor device 102 may be initialized. In one implementation, initialization may commence responsive to connection of the sensor device 102 to the cradle 106, which is connected to the computing device 108. At 504, the sensor device 102 is clipped or otherwise affixed to an object, such as an article of clothing. For example, the user may clip the sensor device 102 to their footwear 104. At 506, the sensor device 102 begins acquiring data from the one or more sensors 302. These sensors 302 may provide information about the user, the surrounding environment, or both.

At 508, a determination is made whether the sensor device 102 is to continue acquiring data. In some implementations, if the user has not made any movement within a certain amount of time, the sensor device 102 may stop acquiring data about the user and the surrounding environment. In other implementations, if the sensor device 102 has little or no power, such as 1% or less of total capacity, the sensor device 102 may discontinue data acquisition. If a determination is made to continue acquiring data, the process returns to 506. If a determination is made to stop acquiring data, the process proceeds to 510 where the sensor device 102 stops acquiring data about the user and the surrounding environment.

At 512, the sensor device 102 is removed from the object. For example, the sensor device 102 may be unclipped from the user's footwear 104.

At 514, the sensor device 102 is coupled to the computing device 108 via the cradle 106. For example, the sensor device 102 may connect electrically to the cradle 106 using a microUSB connector. The cradle 106 acts to establish a connection to the computing device 108 or another device.

At 516, the acquired data 110 is transferred from the sensor device 102 to the computing device 108 or another device such as the server 112 or the other computing devices 114.

At 518, the computing device 108 or other device, processes the acquired data 110 to produce processed data 116. For example, the acquired data 110 may be decompressed, parsed, filtered, information therein subjected to statistical or other analysis, and so forth.

At 520, the processed data 116 may be provided to another device. For example, information about a user's performance on the basketball court may be provided to the user by way of a smartphone, tablet, or other device. The user may use this information to adjust their playing style, adjust a training regimen, and so forth. This data may be distributed, synchronized, or otherwise provided to other devices.

The processed data 116 may be analyzed to provide information about, but is not limited to, one or more of:
1) Audience or crowd assessment of player performance
2) Location of the activity, such as position on a court or playing field, latitude and longitude, altitude, and so forth
3) Ambient temperature
4) Ambient wind speed
5) Ambient air pressure
6) Wind chill 7) Number of steps
8) Amount of play time
9) Direction of play
10) Number of breaks
11) Total time on breaks
12) Number of jumps
13) Information about layups
14) Type of running (for example, fast or slow as designated by threshold speeds, individual user parameters, global parameters for all users, and so forth)
15) Speed of motion In some implementations, information about the object or article of clothing may be used to generate the processed data 116, analysis of the processed data 116, and so forth. For example, information about the weight, size, shape, and so forth, of the footwear 104 may be used.

Information may be provided to the user, other users, coaches, doctors, trainers, teachers, and so forth. This information may include, but is not limited to, one or more of:

1) Past performance sorted by time
2) Goal setting per metrics, Example: reduce the number of breaks and increase the number of layups
3) Locations where the performance is good and bad
4) Crowd energy impact when on road and at home
5) Impact when playing on bench
6) Impact of timeouts
7) Direction of play suited for play style
8) Position on the court more impactful
9) Areas of improvement by providing targeted metrics Information may be provided for a single user, for a group of users (such as a team), and so forth. Information may be aggregated, anonymized, or otherwise processed. The user may specify what information (if any) to share with others. For example, user preferences may specify that information indicating "number of jumps" may be shared, but "resting time" is not.

Figure 6:
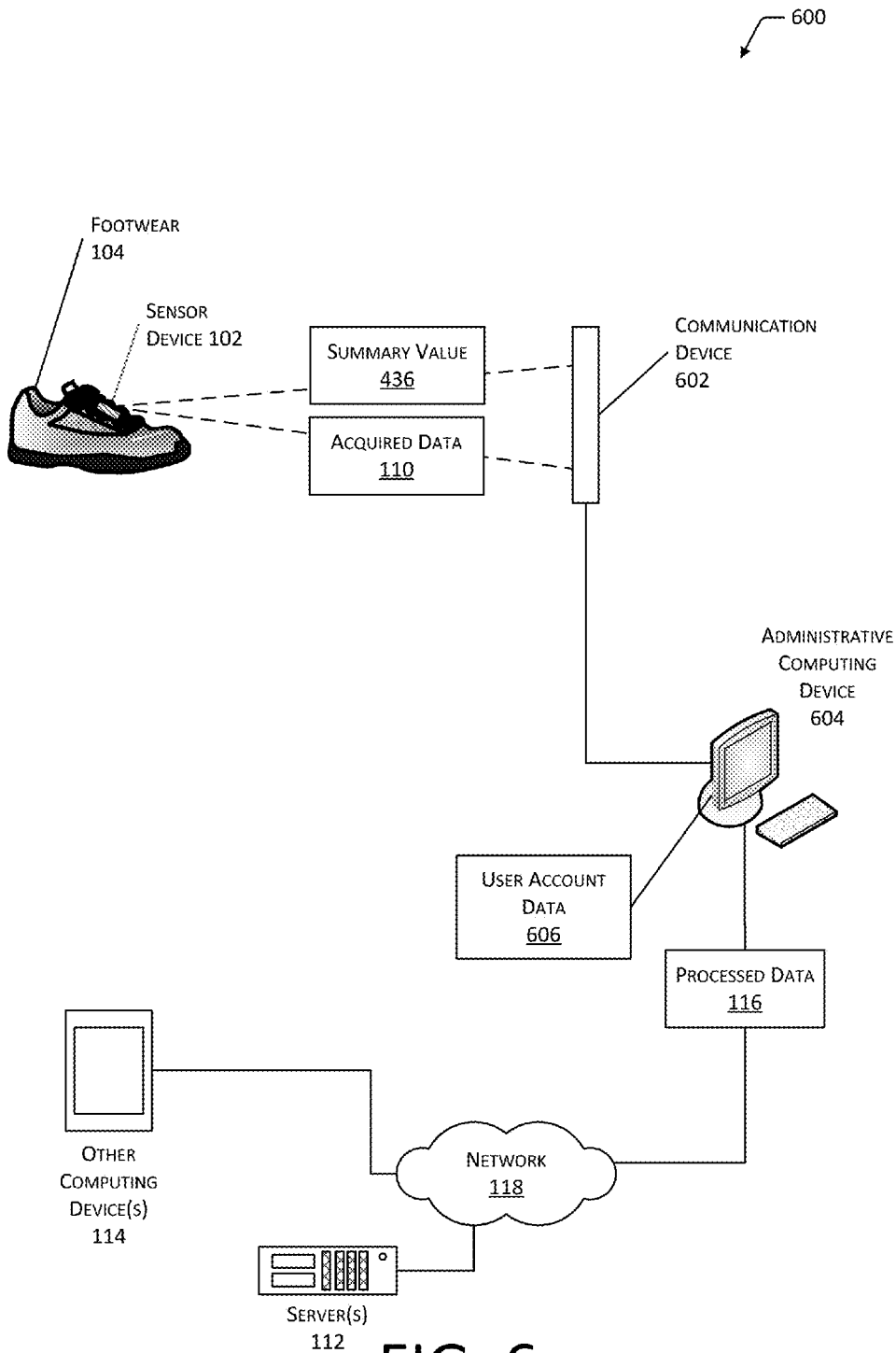
FIG. 6 illustrates a system for acquiring data from the sensor device and processing information with an administrative computing device to assess the performance of one or more users, according to some implementations.

FIG. 6 illustrates a system 600 for acquiring data from a sensor device 102 and processing information with an administrative computing device to assess the performance of one or more users, according to some implementations. In this illustration, the sensor device 102 is affixed to an object such as footwear 104. A communication device 602 communicates with the sensor device 102 wirelessly to transfer information. The communication device 602 may use acoustic, optical, electromagnetic, or other mechanisms to establish communication.

In one implementation, the sensor device 102 and the communication device 602 may use Bluetooth®, Wi-Fi®, or other radio frequency wireless protocols to transfer data.

In one implementation, the sensor device 102 may modulate light emitted by the single element output device 208 to encode the summary value 436 and the device identifier. For example, the sensor device 102 may use pulse width modulation (PWM) to modulate the single element output device 208 to transmit the summary value 436 and the device identifier. The communication device 602 may comprise a detector such a camera or photodetector that is able to detect the modulated light. Electronics in the communication device 602 may be used to demodulate the modulated light from the sensor device 102.

The communication device 602 may be coupled to or may be part of an administrative computing device 604. The administrative computing device 604 may use the communication device 602 to send instructions to the sensor device 102, receive data from the sensor device 102, or both. For example, the administrative computing device 604 may generate a request that is transmitted by the communication device 602 to the sensor device 102. Responsive to the request, the sensor device 102 may transmit to the communication device 602 one or more of the summary value 436, information indicative of the sensor device 102 such as a device identifier, the acquired data 110, and so forth.

The administrative computing device 604 may access other information such as user account data 606. The user account data 606 may comprise information such as a user identification, user name, device identifier of a sensor device 102 that is associated with the user, previously received summary values 436, previously received acquired data 110, and so forth. The user account data 606 may associated a particular device identifier with a particular user account. The administrative computing device 604 access may use the user account data 606 to determine the user account based on the device identifier. A last received summary value 436 may be stored with previously received summary values 436 to determine information such as if the performance of the user has changed, how it has changed, and so forth.

The administrative computing device 604 may generate processed data 116 that may be associated with a particular user account. The administrative computing device 604 may generate a report indicative of the user identification and one or more of the summary values 436 associated with the user account. For example, the sensor devices 102 may be issued to students in a physical education class. The device identifier associated with each of the sensor devices 102 may be associated with the user account for each of the students. As each student returns to the locker room, they may pass through a portal that includes one or more communication devices 602. The communication devices 602 may receive summary values 436 and device identifiers from the sensor devices 102 as they pass through the portal. This information may then be provided to the administrative computing device 604, such as a teacher's desktop computer or tablet. The device identifier may be used to determine a particular user account. The processed data 116 may comprise a summary report listing each of the students and what their respective total performance was, based at least in part on the summary value 436.

Figure 7:
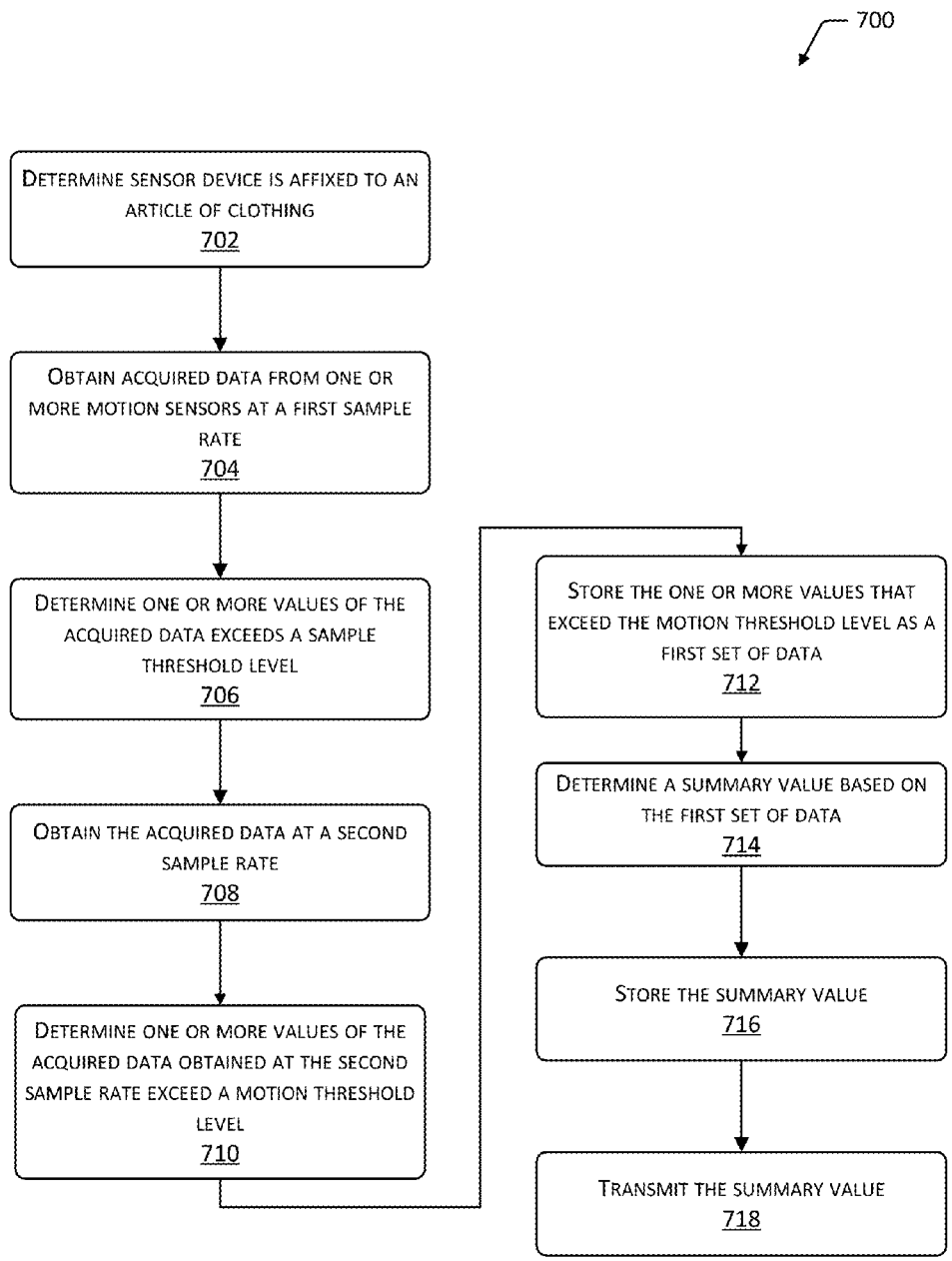
FIG. 7 illustrates a flow diagram of another process to acquire data using the sensor device, according to some implementations.

FIG. 7 illustrates a flow diagram 700 of another process to acquire data using the sensor device 102, according to some implementations. The process may be performed at least in part by one or more of the sensor device 102, the computing device 108, the server 112, the administrative computing device 604, and so forth.

At 702, the sensor device 102 is determined to be affixed to an article of clothing. For example, the attachment sensor 204 may indicate that the attachment mechanism 206 has transitioned from an opened to a closed state. In another example, the attachment sensor 204 may indicate the proximity of an object.

At 704, the acquired data 110 is obtained from one or more sensors 302 at a first sample rate.

At 706, one or more values of the acquired data 110 are determined to exceed a sample threshold level. For example, the sample threshold level may indicate a minimum level of activity that may be used to generate acquired data 110.

At 708, the acquired data 110 is obtained at a second sample rate. In some implementations, the second sample rate is greater than the first sample rate. The sensor device 102 may transition between different sample rates to conserve electrical power, minimize memory consumption, and so forth. The transition may be responsive to the determination of 706.

At 710, the one or more values of the acquired data 110 obtained at the second sample rate are determined to exceed a motion threshold level. For example, the motion threshold level may indicate a minimum level of activity that is deemed to be worth accumulating in the memory 416. Continuing the example, the motion threshold level may be configured to filter out walking, but include running or jumping. In some implementations, the sample threshold level and the motion threshold level may be the same.

At 712, the one or more values that exceed the motion threshold level are stored as a first set of data in the memory 416.

At 714, a summary value 436 based on the first set of data is determined. The summary value 436 may be indicative of a movement of the sensor device 102.

At 716, the summary value 436 is stored in the memory 416 of the sensor device 102.

At 718, the summary value 436 is transmitted to one or more external devices. The external device may include the computing device 108, the server 112, the administrative computing device 604, and so forth.

In some implementations, transmission of summary value 436 may be responsive to receipt of a request. For example, the sensor device 102 may receive from the administrative computing device 604 a request for the summary value 436. Responsive to this request, the sensor device 102 may then send data comprising the summary value 436 to the administrative computing device 604. Other data may be included in the transmission, such as a device identifier indicative of the particular sensor device 102.

In some implementations, the one or more values of acquired data 110 may be determined to be less than the sample threshold level. The storing of the one or more values may be discontinued, and rate of obtaining the acquired data 110 may be transitioned from a first sample rate to a second sample rate. The second sample rate may be less than the first sample rate.

The processes discussed in this disclosure may be implemented in hardware, software, or both hardware and software. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMS), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A device comprising:
a mechanism to affix the device to footwear of a user;
a reset button;
a battery;
one or more motion sensors to obtain acquired data, wherein the one or more motion sensors include an accelerometer and a gyroscope;
one or more sensors to obtain the acquired data indicative of an environment proximate to the device;
a light-emitting diode;
a memory storing computer-executable instructions; and
a hardware processor to execute the computer-executable instructions to:
obtain, at a first time, the acquired data at a first sample rate, wherein the acquired data includes first information about a motion of the device and second information about the environment proximate to the device;
determine one or more values of the acquired data exceeds a sample threshold level;
obtain, at a second time after the first time, the acquired data at a second sample rate, wherein the second sample rate is greater than the first sample rate;
determine one or more values of the acquired data obtained at the second sample rate exceed a motion threshold level;
store the one or more values that exceed the motion threshold level as a first set of data in the memory;
determine a summary value based on the first set of data, wherein the summary value is indicative of a movement of the device;
store the summary value in the memory; and
transmit the summary value to an administrative computing device.

2. The device of claim 1, further comprising computer-executable instructions to:
determine the summary value is less than a minimum threshold value;

activate the light-emitting diode to emit a first color, based on the summary value being less than the minimum threshold value;

determine the summary value is greater than the minimum threshold value and less than an intermediate threshold value;

activate the light-emitting diode to emit a second color, based on the summary value being greater than the minimum threshold and less than an intermediate threshold value;

determine the summary value is greater than the intermediate threshold value; and activate the light-emitting diode to emit a third color, based on the summary value being greater than the intermediate threshold value.

3. The device of claim 1, further comprising computer-executable instructions to reset the device, wherein the reset is initiated by one or more of:

activation of the reset button, or expiration of a reset time period; and further wherein the reset includes disregarding the stored first set of data and the summary value in the memory.

4. A device comprising:

a mechanism to affix the device to a user;
  a motion sensor to obtain motion data indicative of motion of the device;
  one or more sensors to obtain environment data indicative of an environment proximate to the device;
  a memory storing computer-executable instructions; and
  a hardware processor configured to execute the computer-executable instructions to:
  obtain, at a first sample rate, the motion data indicative of the motion of the device and the environment data indicative of the environment proximate to the device;
  determine one or more values of the motion data exceed a motion threshold level;
  store the one or more values of the motion data that exceed the motion threshold level as a first set of data in the memory;
  generate a summary value based on the first set of data; and
  store the summary value and the environment data in the memory.

5. The device of claim 4, further comprising computer-executable instructions to:

determine one or more values of the motion data are less than the motion threshold level;

discontinue the storing of the one or more values; and obtain the motion data and the environment data at a second sample rate, wherein the second sample rate is less than the first sample rate.

6. The device of claim 4, further comprising computer-executable instructions to:

send the summary value and the environment data to an administrative computing device.

7. The device of claim 4, further comprising a single element output device, the single element output device further includes one or more colors and further comprising computer-executable instructions to:

determine the summary value is less than a minimum threshold value of the motion of the device;

activate the single element output device to emit a first color;

determine the summary value is greater than the minimum threshold value and less than an intermediate threshold value of the motion of the device;

activate the single element output device to emit a second color;

determine the summary value is greater than the intermediate threshold value; and activate the single element output device to emit a third color.

8. The device of claim 4, further comprising computer-executable instructions to reset the device, wherein the reset includes one or more of:

activation of a button; or expiration of a reset time period;

and further wherein the reset includes:

disregard the first set of data that exceed the motion threshold level and the summary value; and obtain the motion data and the environment data at one of the first sample rate or the second sample rate.

9. The device of claim 4, wherein the device further includes:

an attachment mechanism to attach the device to footwear, the mechanism including one or more of:
  a magnet,
  a hook and loop fasteners,
  a clip, or
  a loop;
an attachment sensor proximate to or integrated with the attachment mechanism, wherein the attachment sensor is configured to generate status data indicative of one or more of:
  proximity of the footwear,
  proximity of the user,
  the attachment mechanism is in a closed state, or
  the attachment mechanism is in an open state; and
further comprising computer-executable instructions to:
  store the status data in the memory.

10. The device of claim 4, the motion sensor comprising one or more of:

an accelerometer, a gyroscope, a magnetometer, or a radionavigation device.

11. The device of claim 4, the device further comprising:

a power source including one or more of:
  a battery,
  a capacitor, or
  a fuel cell.

12. The device of claim 4, the single element output device comprising one of:

light-emitting diode, electroluminescent element, an incandescent lamp, a fluorescent lamp, a quantum dot, an electrophoretic element, or a cholesteric element.

13. The device of claim 4, the device further comprising:

a power source including a recharging device comprising one or more of:
  one or more electrical contacts, or
  a wireless power receiver.

14. A system comprising:

a wearable motion tracking device, wherein the wearable motion tracking device includes:

a motion sensor to generate acquired data of a user associated with the wearable motion tracking device;

one or more sensors to obtain the acquired data indicative of an environment proximate to the device;

a first memory storing first computer-executable instructions; and a first hardware processor to execute the first computer-executable instructions to:

obtain acquired data from the user associated with the wearable motion tracking device at a first sample rate, wherein the acquired data includes first information about a motion of the device and second information about the environment proximate to the device;

determine at least a portion of the acquired data exceeds a first motion threshold level;

based on the acquired data exceeding the first motion threshold level, obtain acquired data from the user associated with the wearable motion tracking device at a second sample rate; store the acquired data at the second sample rate in the memory; determine a summary value of the stored acquired data; and store the summary value in the memory; and an administrative computing device, the administrative computing device comprising: a communication device; a second memory storing second computer-executable instructions; and a second hardware processor to execute the second computer executable instructions to: receive from the wearable motion tracking device the summary value; and store the summary value.

15. The system of claim 14, wherein the administrative computing device further comprises second computer-executable instructions to:

generate a request for the summary value; and send the request to one or more wearable motion tracking devices.

16. The system of claim 14, wherein the administrative computing device further comprises second computer-executable instructions to:

store the summary value in a corresponding user account associated with the wearable motion tracking device, wherein the user account includes:

user identification; and information based at least in part on previously stored summary values associated with the user account.

17. The system of claim 14, wherein the administrative computing device further comprises second computer-executable instructions to:

generate a report indicative of a user identification and one or more summary values associated with a user account.

18. The system of claim 14, wherein the administrative computing device further comprises second computer-executable instructions to:

establish, using the communication device, wireless communication with the wearable motion tracking device; and receive, using the communication device, the summary value from the wearable motion tracking device.

19. The system of claim 14, wherein the wearable motion tracking device further includes a single element output device, wherein the single element output device emits one or more colors based on the summary value.

20. The system of claim 14, wherein the administrative computing device further comprises second computer-executable instructions to:

receive from the wearable motion tracking device a device identifier;

determine a user account based on the device identifier; and compare the received summary value with previously received summary values associated with the user account.

* * * * *